United States Patent [19]

Persidsky

[11] 4,322,298
[45] Mar. 30, 1982

[54] CENTRIFUGAL CELL SEPARATOR, AND METHOD OF USE THEREOF

[75] Inventor: Maxim D. Persidsky, San Francisco, Calif.

[73] Assignee: Advanced Blood Component Technology, Inc., San Francisco, Calif.

[21] Appl. No.: 269,379

[22] Filed: Jun. 1, 1981

[51] Int. Cl.³ ............................................. B01D 21/26
[52] U.S. Cl. ..................................... 210/787; 210/516; 210/927; 233/26; 128/214 D
[58] Field of Search ............... 210/787, 516, 927, 359, 210/790, 304, 512.1, 512.2; 233/26; 128/214 D

[56] References Cited

U.S. PATENT DOCUMENTS 4,268,393 5/1981 Persidsky et al. ................... 210/927
4,269,718 5/1981 Persidsky ............................ 210/787

Primary Examiner—Benoît Castel
Attorney, Agent, or Firm—Limbach, Limbach & Sutton

[57] ABSTRACT

This invention relates to a method and apparatus for the fractionation of a suspension of finely divided solid particles differing in sedimentation velocity, such as platelets and other blood cells. The separation of, for instance, platelet-rich plasma (PRP) from whole blood is accomplished by centrifuging the blood sample in a bag and by injecting into its outer centrifugal end a volume of saline which displaces the PRP from the blood sample after red cells have been sedimented away from the other end of the bag. The preferred apparatus is designed as a closed system of interconnected bags held in a support made to fit a large centrifuge bucket. The flow of liquid is generated by placing the saline-containing bag closer to the center of rotation while positioning the collection bag at a farthest distance from this center. The discharge of PRP from the separation bag into the collection bag is facilitated by making the inner centrifugal end of the separation bag to collapse in response to centrifugal force. PRP in the collection bag is further fractionated into platelet concentrate and plasma at a higher centrifugal force than that for PRP separation.

15 Claims, 58 Drawing Figures

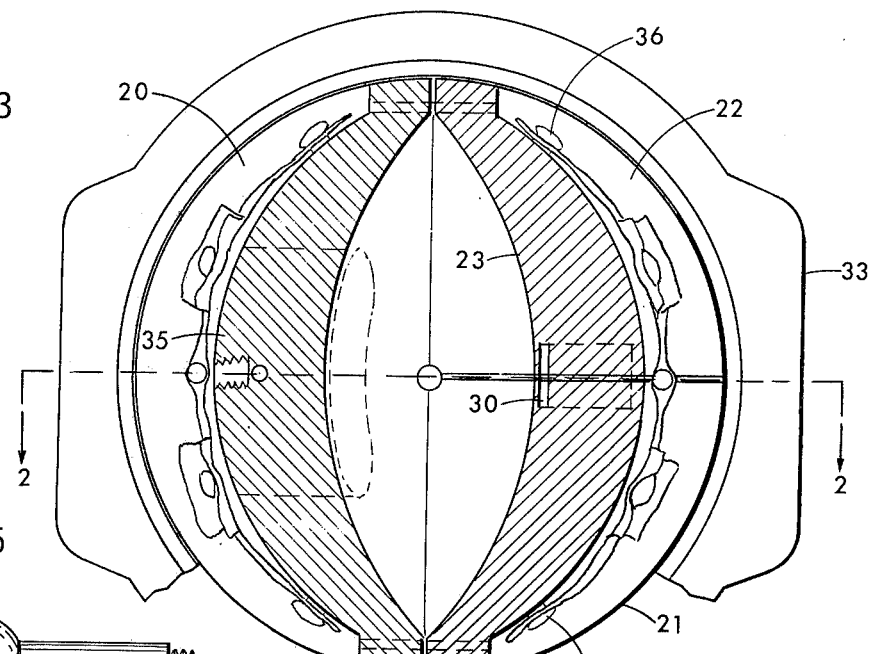
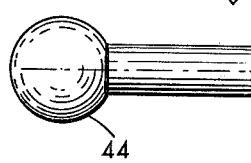
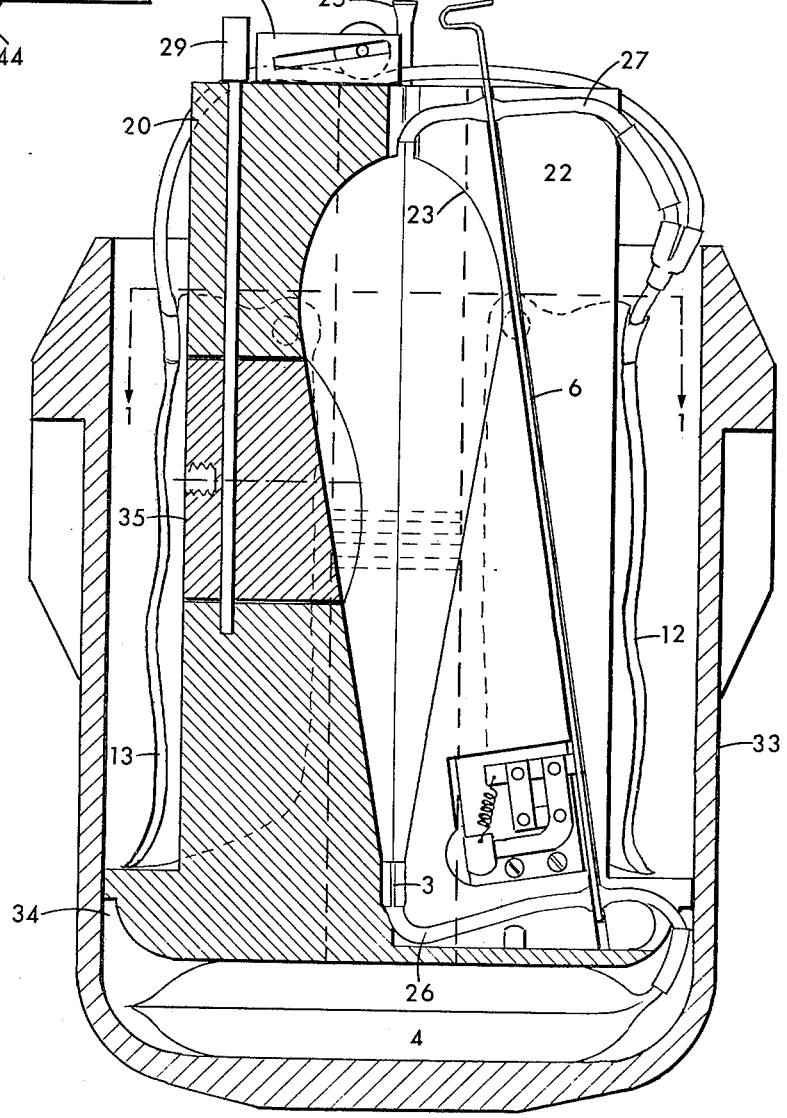

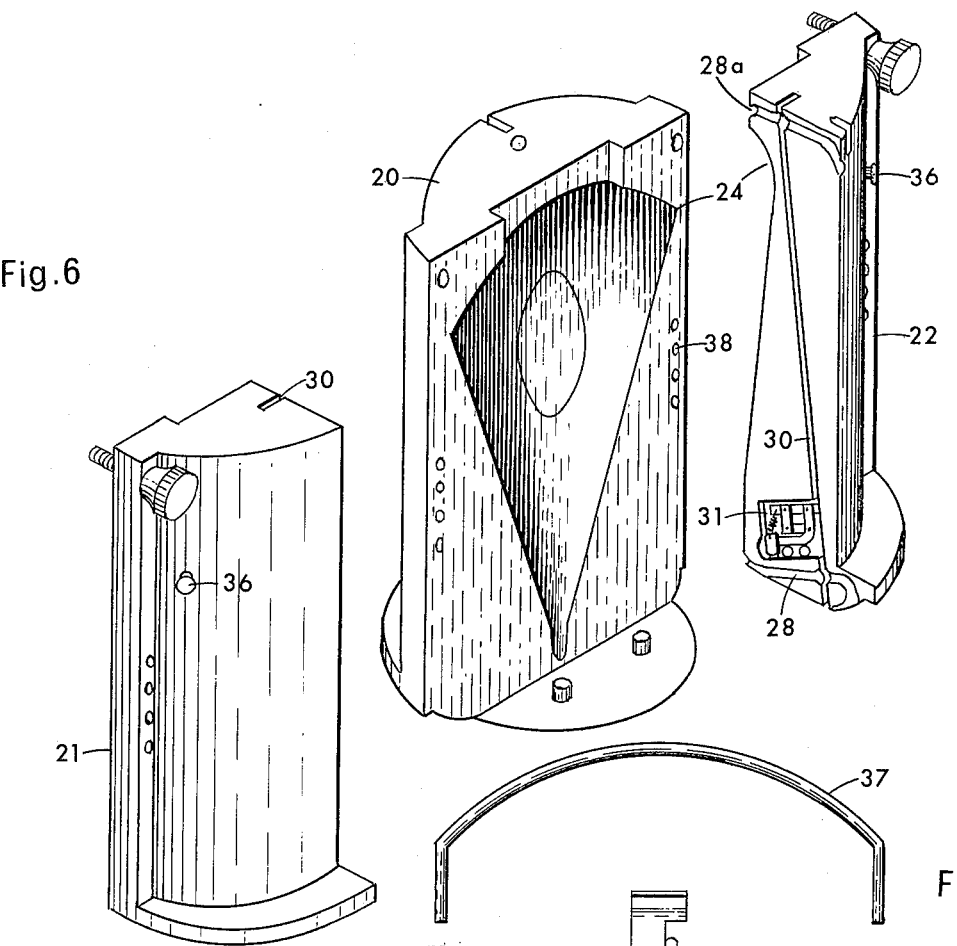
Fig.6
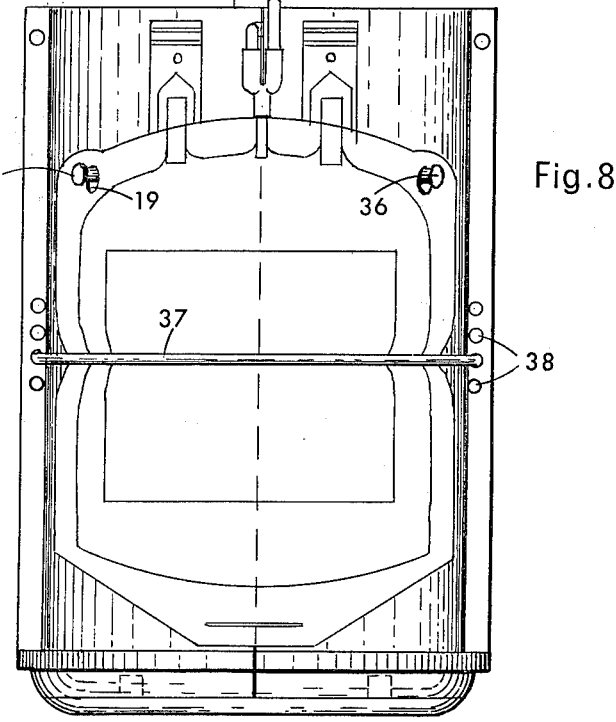
Fig.7
Fig.8
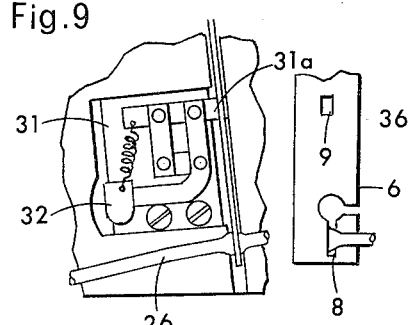
Fig.9
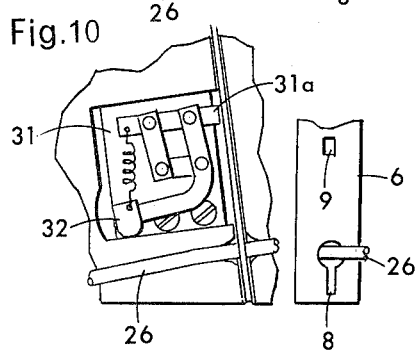
Fig.10

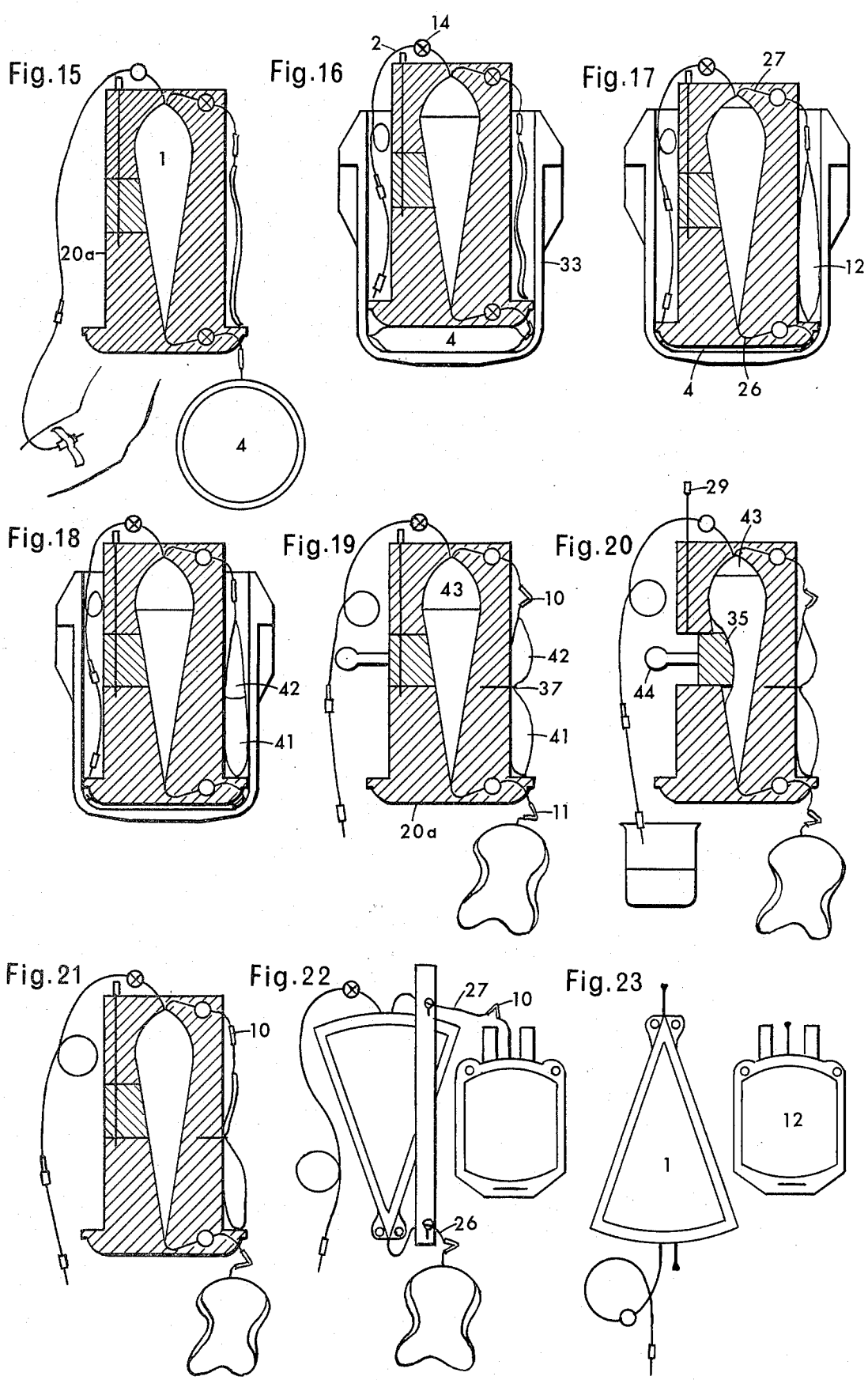

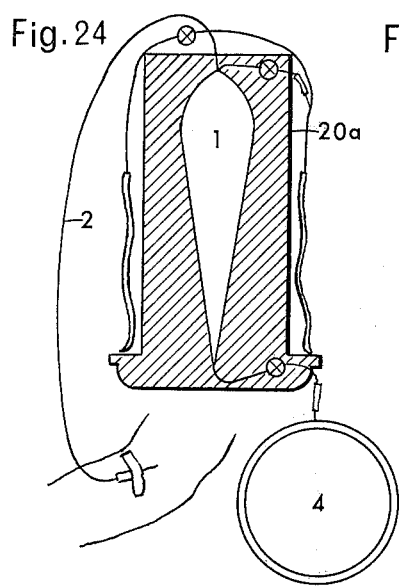
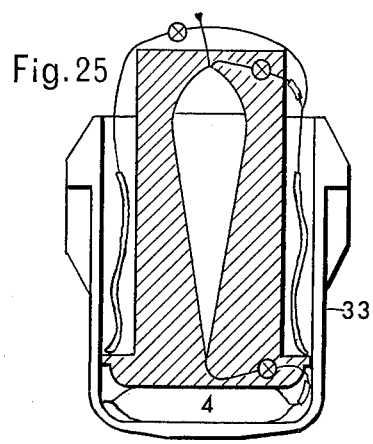
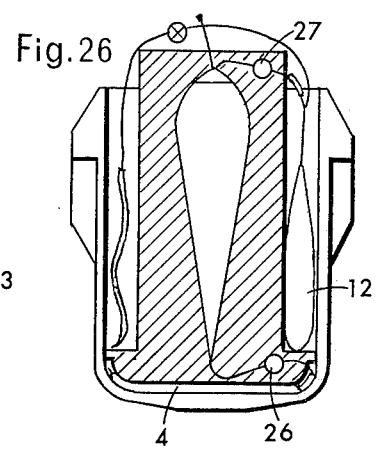
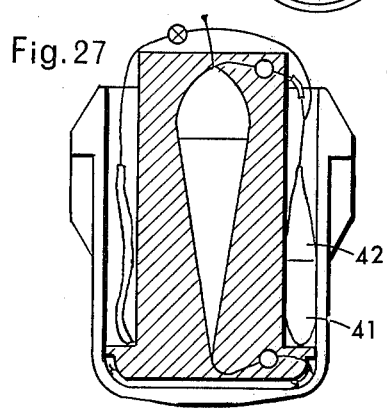
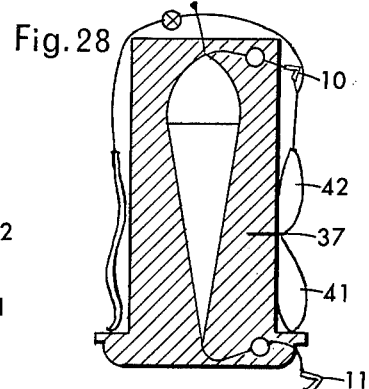
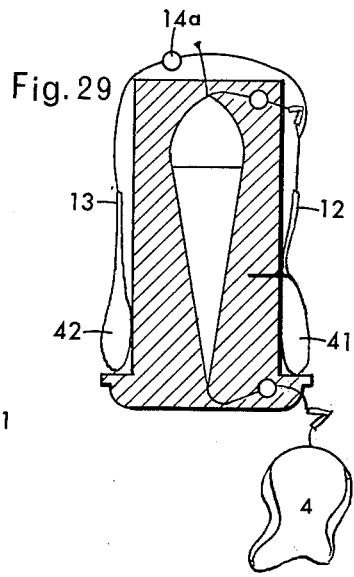
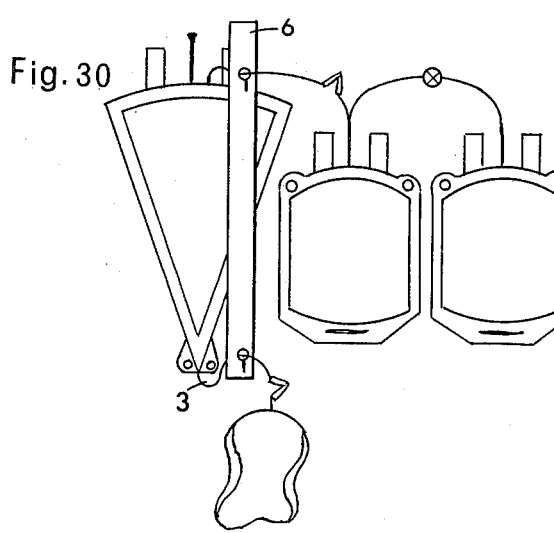
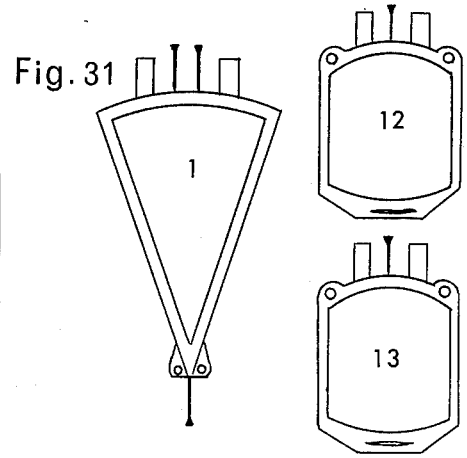

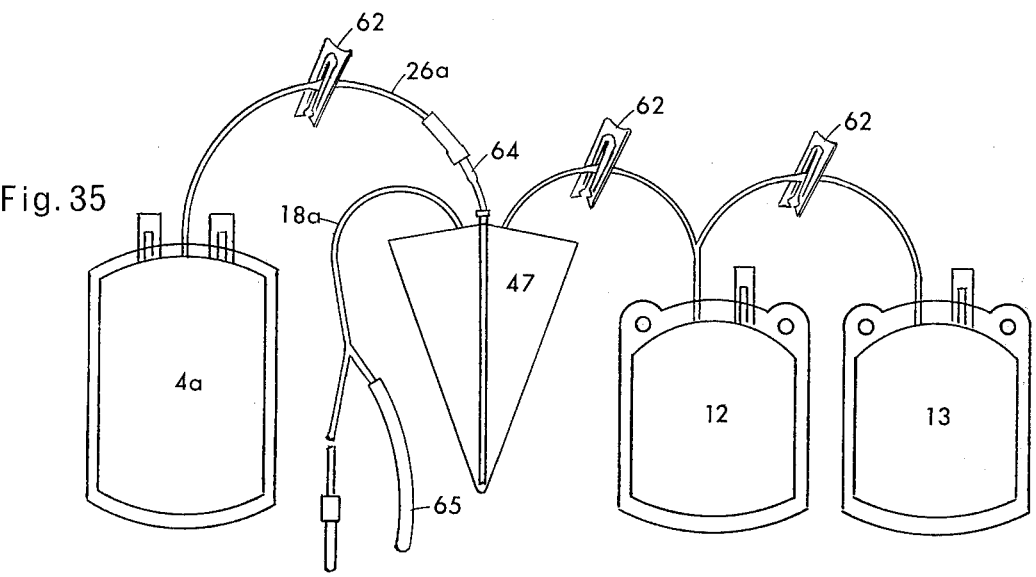
Fig. 35
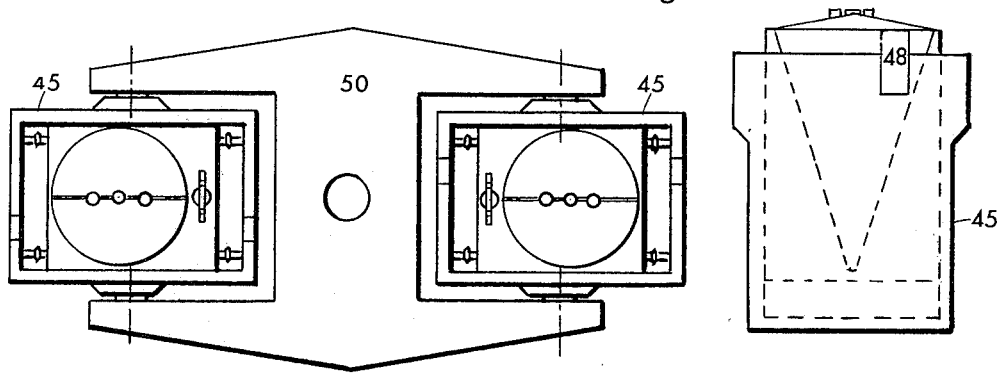
Fig. 36
Fig. 37
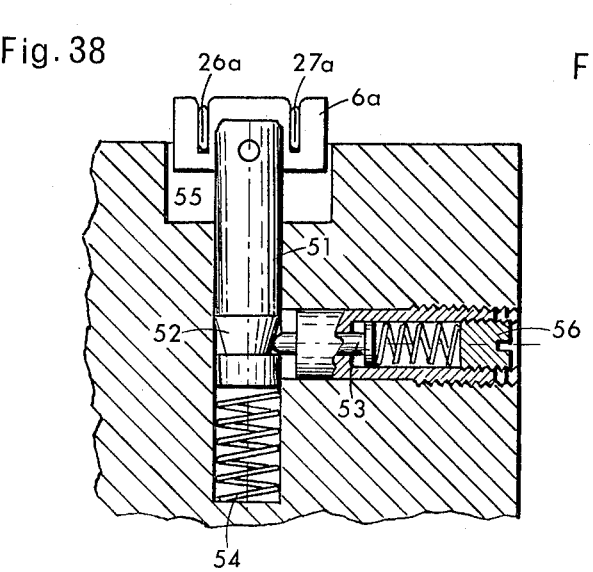
Fig. 38
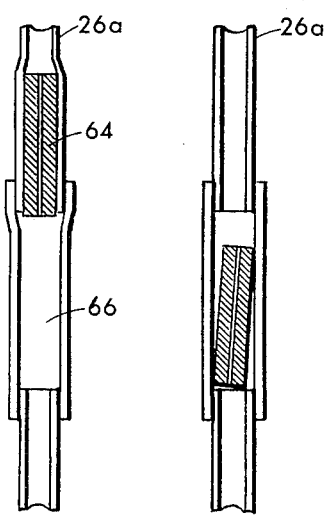
Fig. 39

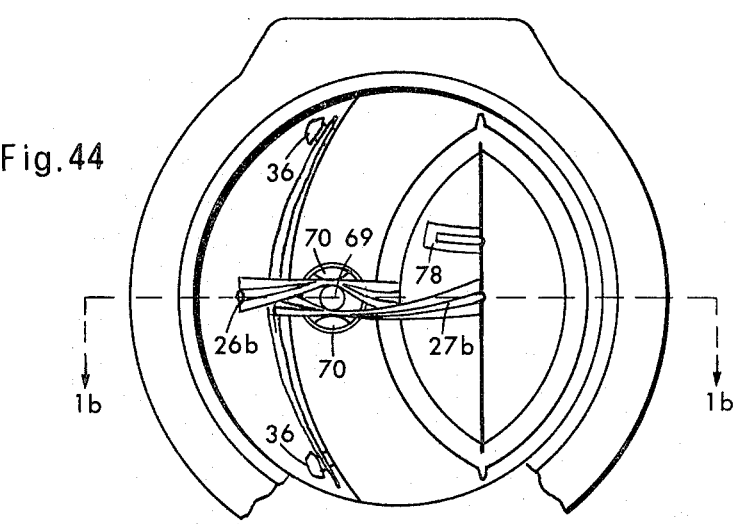
Fig. 44
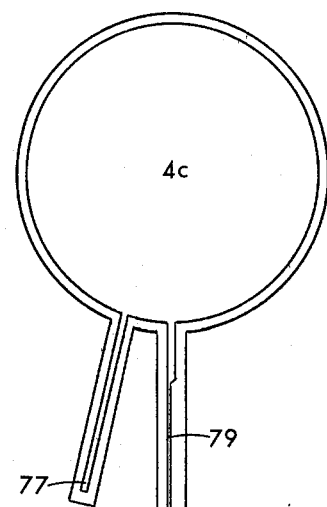
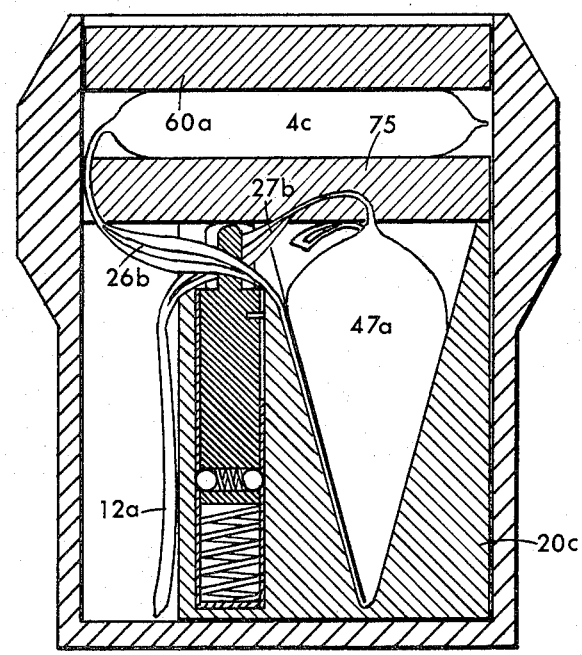
Fig. 45
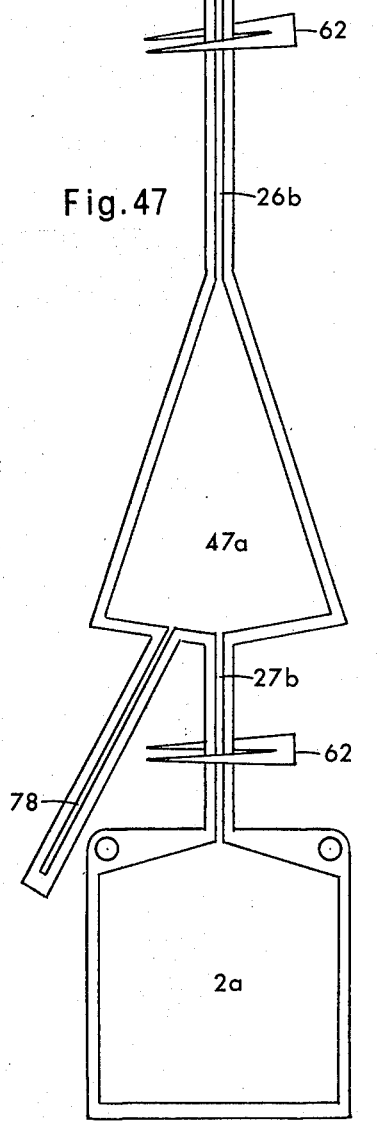
Fig. 47
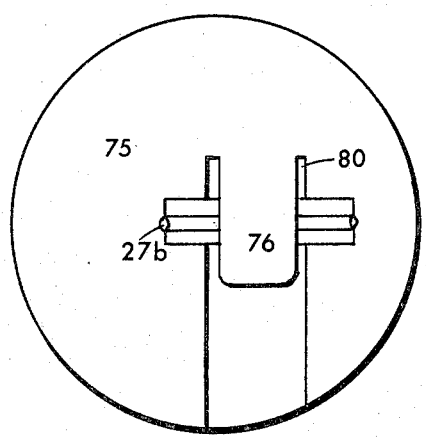
Fig. 46

CENTRIFUGAL CELL SEPARATOR, AND METHOD OF USE THEREOF

BACKGROUND OF INVENTION

The present invention relates to a new centrifugal process and device for harvesting blood platelets for transfusion. The invention provides a means for collection of platelets in a closed, sterile and disposable system and, more particularly, provides a means for procurement of a therapeutically effective dose of platelets from a single donor, as well as from multiple or random donors. This invention is an improvement of the invention, disclosed in two U.S. patents: one by Maxim D. Persidsky entitled "Process and Device for Centrifugal Separation of Platelets," U.S. Pat. No. 4,269,718, issued on May 26, 1981, and the other by Maxim D. Persidsky and Nan-Sing Ling entitled "Apparatus for Centrifugal Separation of Platelet-Rich Plasma," U.S. Pat. No. 4,268,393, issued on May 19, 1981.

Among the problems encountered in the blood component separation technology currently employed in harvesting platelets for transfusion are: low collection yield of platelets; loss of large, dense platelets (designated herein as young platelets); high contamination of collected platelets with white blood cells (WBCs); sterility problem associated with the automated plateletpheresis systems; long processing time; and high equipment and operational cost. In spite of these shortcomings, there is a growing demand for transfusion of platelets for treatment of bleeding in thrombocytopenic and thrombocytopathic patients. Transfusion of platelets is also used as replacement therapy in patients with a temporary depletion of platelets due to acute leukemia, chemotherapy, radiation therapy, and major surgical procedures. As a result, within the past decade the number of platelet units transfused annually has expanded enormously. In 1971, 413,500 platelet units were transfused in the U.S. From the survey of blood collection by AABB institutional members, more than 1,250,000 units of platelets were transfused in 1975. According to the present estimate, there will be at least 3,500,000 units of platelet concentrates transfused in the U.S. during 1980.

The process for centrifugal collection of platelets as disclosed in the two above cited U.S. patents, has the potential to resolve all the above mentioned problems. This process, representing a new type of manual plateletpheresis, was evolved from the process of centrifugal elutriation (CE). Although it bears some similarities to CE, it is different from CE in several important aspects. The separation of various size particles by CE is accomplished by the process of washing particles in the separation chamber with an exponential flare at its broad end which is oriented toward the center of rotation. Liquid medium is flowing through this chamber in the direction against the centrifugal force and forms a gradient of rapidly decreasing flow along this direction. Smaller and less dense particles are continuously washed out from the chamber while larger and denser particles are retained at various levels of their equilibria within the gradient of liquid flow. A large volume of medium is required during the separation of particles by CE.

In an experimental study using the platelet collection device in the form of either FIG. 1 or FIGS. 2 to 4 of the U.S. Pat. No. 4,269,718, platelets were harvested from whole human blood at about 90% recovery of the total blood platelets. With a chamber of 11 ml capacity of FIG. 1, the time required to separate platelet-rich plasma (PRP) from whole blood was 3 minutes while with a larger chamber of 21 ml capacity of FIGS. 2 to 4, it was 5 minutes. No WBC per $10^6$ cells counted was found under the microscope in PRP samples separated by either chamber. The morphology and size distribution of these platelets appeared to be similar to platelets in the control smears of whole blood. The release of adenosine triphosphate (ATP) from these platelets was on the average 33% higher than that from platelets prepared by differential centrifugation. Platelets harvested either by the differential centrifugation or by the process of the present invention were found to be similar in aggregation response induced by adenosine diphosphate (ADP) or epinephrine and similar in their serotonin secretion. In vivo study of survival of radioactive chromium-labeled autologous platelets in rabbits yielded similar results for both preparations.

Preliminary tests of the scaled-up PRP separation system of 220 ml capacity built in accordance with the design of FIG. 9 of the U.S. Pat. No. 4,268,383, yielded results similar to those obtained with the systems of smaller capacity. Platelet recovery was close to 90% of the total platelets and no WBC was detected per $10^6$ cells counted. The platelet morphology was found to be normal. With this system of 220 ml capacity, the time used to separate PRP took 8 to 10 minutes.

The increased release of ATP by platelets harvested with the 11-ml system can be attributed to the presence of a larger number of recovered young platelets. Young platelets are known to contain higher concentration of ATP in their granules than the old platelets. The recovery of young platelets in these preparations is further substantiated by the above morphological observations.

According to a process and device of the present invention, a conical chamber is used for the separation of PRP. The chamber is loaded with whole blood prior to centrifugation. Then it is subjected to a short period of centrifugation in order to induce the formation of a narrow zone of clear plasma at the broad end of the chamber. Thereafter, a small volume of normal saline, equivalent to that of blood plasma, is pumped gradually into the chamber at its vertex in the direction against the centrifugal force. By this action, saline filters through the loosely packed blood cells and displaces PRP while red blood cells (RBCs) and white blood cells are retained in the chamber with the aid of centrifugal force at a steady state equilibrium. Under the above conditions, blood cells form a dense cells suspension which behaves like a fluidized bed of clay particles used in industrial furnaces. This dense cell suspension acts as a depth filter which allows platelets to pass through while holding back all the other cell constituents. Thus, this process of PRP separation can be distinguished from CE in that it consists of two processes: one is the displacement process; and the other is the filtration process; whereas CE involves the process of differential washing. The PRP separation process, referred to above in the two U.S. Patents, requires only a small volume of liquid for the displacement of PRP. Therefore, it was possible to design a self-sufficient device to fit in a swinging centrifuge bucket. This device includes a collapsible container for liquid medium, a centrifugally operated pump, a separation chamber, and a collection compartment.

In addition, the present process does not involve pelleting of blood cells as it does in the case of differential centrifugation. Pelleting may release ADP from RBCs which can in turn cause platelet aggregation. Therefore, platelets harvested by the present process should be less damaged than those obtained with the differential centrifugation method.

The present system with its high collection yields of platelets and its capability to recover young platelets can potentially be of great value in transfusion service when it is fully developed. It is known that young platelets can survive longer and are expected to be more effective hemostatically than old platelets. In addition, the apparent absence of WBC in the platelets harvested by the present system would be desirable in reducing the risk of immunological complications by WBCs after repeated platelets transfusions.

All the devices illustrated in both U.S. Patents represent an open system and therefore the problems of maintaining sterility still remain.

SUMMARY OF INVENTION

A principal object of the present invention is to provide a closed system of flexible bags for harvesting platelets having a sterile, non-pyrogenic fluid path which will fully satisfy the FDA requirements of safety for human use.

Another object is to provide a system of the character stated that is capable of harvesting a therapeutically effective dose of platelets from a single donor as well as from multiple donors.

A further object is to provide a system of this type which is highly efficient and capable of harvesting PRP containing functionally normal platelets, without loss of young platelets, and free of white blood cells.

Another object is to provide a system of this type which is capable of fractionating whole blood into packed red cells, platelet concentrate (PC), and platelet-poor plasma (PPP) by means of an uninterrupted centrifugation procedure, thus reducing the handling and processing time to a minimum.

Also, an object is to provide a system of the above characteristics which is simple, economical, disposable, and easy to operate.

It will become apparent as this description progresses that the invention is not limited in application to harvesting platelets, but may be used to equal advantage in the separation of blood plasma, in the preparation of red blood cells for liquid storage or for cryopreservation, and for washing red blood cells, as well as for the removal of cryoprotective agents such as hydroxyethyl starch from thawed red blood cells or other types of cells prior to their transfusion or use. Other possible applications of this invention include aseptic processing of cells in tissue culture such as replacement of culture media, cell washing and harvesting.

According to the present invention, the apparatus is designed to fit in a swinging bucket of a centrifuge as an insert consisting of a closed, disposable multiple bag system which is held in a rigid support. Two such systems of bags are provided depending on the usage: one system for harvesting platelets from single donor consists of a triple bag unit, and the other system for multiple donors consists of a quadruple bag unit. Both units include a round bag, a triangular bag, and either one or two square bags depending on the above specified designation. A round bag is used for holding a displacing liquid medium. A triangular bag functions as a separation chamber, and square bags for collection of PRP, PC and PPP. The triangular bag has a concave profile and is enclosed in a rigid support with a correspondingly shaped cavity, so that when it is filled with blood, it assumes the shape of a flattened cone. The square bags are placed in the side pockets of the rigid support at the same distance as the triangular bag from the center of rotation. Such an arrangement of the square collection bags in relation to the position of the triangular separation bag represents an important improvement in the design of the present embodiment as compared to that described in the two earlier U.S. Patents. The present embodiment allows one to further separate PRP into PC and PPP by simply increasing the centrifugation speed. Thus, the platelet harvesting procedure of the present invention consists of a sequence of three consecutive centrifugation steps, each subsequent step being carried out at increased speed of rotation. In contrast, the earlier design has the collection container placed immediately above the centripetal end of the separation chamber. With such an arrangement it is necessary to remove the collection container with PRP from the apparatus and to transfer it into another centrifuge for further processing. As in the previous systems, the flow of displacing liquid through the triangular bag is generated by the centrifugal force. This is accomplished by placing the round bag containing the liquid medium underneath the rigid support in a centrifuge bucket so that during centrifugation the support compresses the round bag. As a result, the medium from the round bag is flowing via a short piece of capillary tube at its vertex into the triangular bag in the direction against the centrifugal force. The capillary tube with appropriately selected lumen is used to control the rate of fluid flow. As in the prior systems, a valve mechanism actuated by the centrifugal force is used for controlling entry of fluid flow into the triangular bag. It is different from the previously described mechanisms in that the flow controlling valve is designed as two pinch clamps in the form of two key-hole slots in a metal strip which simultaneously pinch the two tubes, one leading to and the other coming from the triangular bag. A specially designed latch mechanism holds the strip having both clamps in place until the top of the triangular bag is cleared of red blood cells. By increasing the g force, the latch mechanism is then actuated, thereby releasing both clamps and allowing the flow of medium into the triangular bag.

Another preferred embodiment of the PRP separator is based on a rectangular design of centrifuge swinging bucket. This embodiment enables one to accomodate a separation chamber holding a conical bag of 513 ml capacity in the limited space of standard blood bank centrifuges. It will also accommodate rectangular bag for displacing medium. This rectangular bag can be used as a storage bag for the remaining blood cells after transferring them into it from the conical bag.

Further reduction to practice of this invention is accomplished by providing an improved mechanism for generating flow of displacing medium in response to centrifugal force. According to this preferred embodiment, flow of displacing medium is induced by the gradient of hydrostatic pressure resulting from positioning the bag containing the medium closer to the center of rotation than both the separation and the collection bags, the latter being positioned the farthest distance from this center. This arrangement provides the required differences of the fluid levels in this closed system of interconnected bags which generates flow of liquid from its highest level (closest to the center of rotation) towards its lowest level (farthermost from the center of rotation).

Another improvement of this invention is accomplished by providing the means for displacing PRP from the top of the conical separation bag without causing PRP dilution. This is accomplished by placing the bag containing displacing medium directly on top of the conical bag which causes the conical bag to collapse at its broad end under centrifugal force thereby displacing PRP from its top level via the interconnecting tubing into the collection bag. The displacement volume is controlled by a circular plate situated between the bag with displacing medium and the conical bag. This plate stops inside the rigid conical support at the same diameter as that of the plate. The diameter of the plate is selected to displace maximum PRP from the blood sample on the basis of blood hematocrit.

The apparatus of the present invention represents a closed system having a sterile, non-pyrogenic fluid path. Other more detailed objects and advantages of the invention will appear hereinafter.

BRIEF DESCRIPTION OF DRAWINGS

Referring to the accompanying drawings:

FIG. 3 is an upper cross-sectional view of an embodiment of the blood platelet collection apparatus within a cylindrical centrifuge bucket taken along the line 1—1 of FIG. 4.

FIG. 4 is a longitudinal cross-sectional view of an embodiment of the blood platelet collection apparatus within a cylindrical centrifuge bucket taken along the line 2—2 of FIG. 3.

FIG. 5 is a side elevation of a part representing the handle of a plunger.

FIG. 6 is a perspective view of the three parts of a disassembled triangular bag support.

FIG. 7 is a side elevation of a square bag brace clamp.

FIG. 8 is a side elevation of an embodiment of an assembled triangular bag support having on its front side a collection bag, which is partitioned into two halves by a brace clamp.

FIG. 9 is an enlarged fragmentary side view of a flow controlling valve mechanism shown in a closed position.

FIG. 10 is the same mechanism as above but shown in an open position.

FIG. 15 is a cross-sectional diagrammatic view of an apparatus containing a triple bag unit for a single donor, taken along a vertical central axis and showing a triangular bag being filled with blood collected directly from a donor.

FIG. 16 is a cross-sectional diagrammatic view of the same apparatus as above inserted into a centrifuge bucket and showing clearing at the top of a triangular bag after slow-speed centrifugation.

FIG. 17 is the same apparatus as above after centrifugation at a higher speed than in the preceding step showing both fluid lines leading to and from a triangular bag being open, and showing a round bag collapsed and PRP displaced from the triangular bag into a square bag.

FIG. 18 is the same apparatus as above after centrifugation at a highest speed showing separation of PRP into PC and PPP in a square bag.

FIG. 19 is the same apparatus as above after removal from a centrifuge bucket and showing a square bag being clamped in the mid-portion separating PPP from PC while a fluid line from the square bag is now closed, and showing a handle being attached to a plunger.

FIG. 20 is the same apparatus as above showing a pushed-in position of the plunger and showing supernatant being expelled from the triangular bag into a waste container.

FIG. 21 is the same apparatus as above after PPP has been transferred to the triangular bag containing blood cells.

FIG. 22 is a side view of a triple bag unit removed from a supporting device.

FIG. 23 is a side view of a disconnected and sealed triangular bag containing reconstituted blood fraction ready for reinfusion into the donor, and of a hermetically sealed square bag containing PC.

FIG. 24 is a cross-sectional diagrammatic view of an apparatus containing a quadruple bag unit for multiple donors taken along a vertical central axis and showing a triangular bag being filled with blood from a donor.

FIG. 25 is the same apparatus as above inserted into a centrifuge bucket and showing clearing at the top of a triangular bag after slow-speed centrifugation.

FIG. 26 is the same apparatus as above after centrifugation at a higher speed than in the preceding step showing both fluid lines leading to and from a triangular bag being open, and showing a round bag collapsed and PRP displaced from the triangular bag into a square bag.

FIG. 27 is the same apparatus as above after centrifugation at a highest speed showing separation of PRP into PC and PPP in a square bag.

FIG. 28 is the same apparatus as above after removal from a centrifuge bucket and showing a square bag being clamped in the mid-portion separating PPP from PC while a fluid line coming from a triangular bag and joining with two square bags is being closed.

FIG. 29 is the same apparatus as above after PPP has been transferred to another square bag.

FIG. 30 is a side view of a quadruple bag unit removed from a support.

FIG. 31 is a side view of a disconnected and hermetically sealed bags containing blood fractions ready for storage or for immediate use.

FIG. 35 is a side view of an embodiment of a disposable quadruple-bag unit for harvesting of blood platelets from blood of multiple or random donors.

FIG. 36 is a top elevation of a centrifuge rotor with two square buckets holding two separate units without bags.

FIG. 37 is a side elevation of a centrifuge bucket with a rectangular window.

FIG. 38 is an enlarged portion of a cross-sectional view of an embodiment of a valve release mechanism.

FIG. 39 is a longitudinal cross-sectional view of an on-line flow controlling device shown in two positions: on the left, the capillary tube is inserted on-line in the fluid path; and on the right, the capillary tube is dislodged.

FIG. 44 is a partial top view of another version of the PRP separator shown inside the centrifuge bucket.

FIG. 45 is a cross-sectional view of the above embodiment taken along the line 1b—1b of FIG. 44.

FIG. 46 is a lower elevational view of the supporting plate.

FIG. 47 is a side view of the disposable triple bag unit.

DETAILED DESCRIPTION OF THE INVENTION

The apparatus of this invention is designed as an insert for a centrifuge bucket includes a disposable system of bags with a closed, sterile, non-pyrogenic fluid path. The apparatus is represented in two configurations: one configuration is for harvesting platelets from a single donor and another is for harvesting platelets from multiple or random donors.

Figure 1:
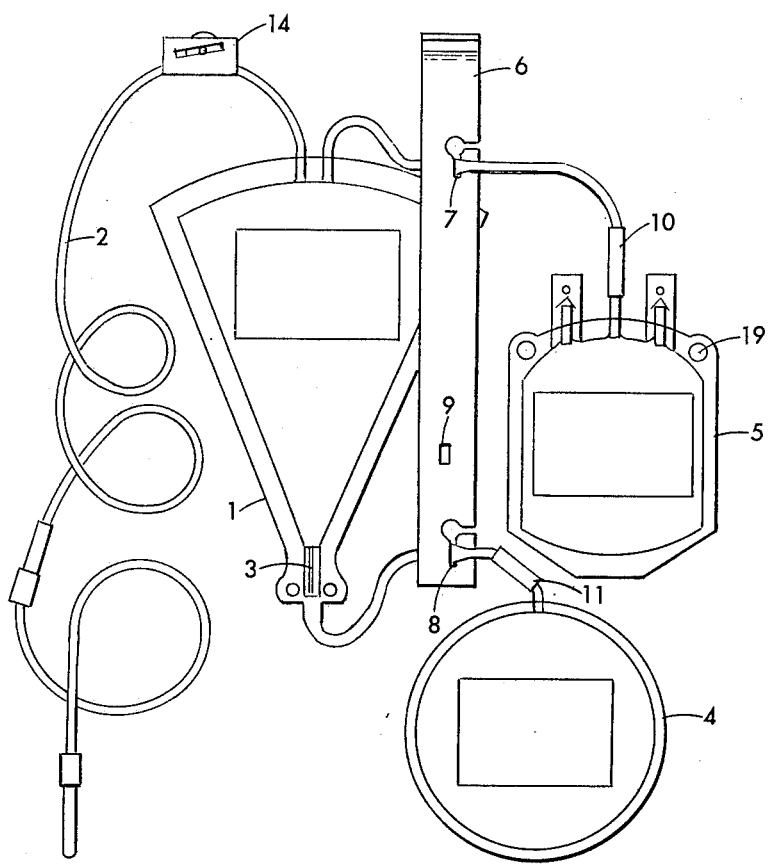
FIG. 1 is a side view of an embodiment of the disposable part of an apparatus consisting of a triple bag unit adapted for separation of blood platelets from a single donor.

The apparatus for use with a single donor, shown in FIG. 1, is a triple bag unit having a triangular bag 1 (designated hereon in Arabic numerals) of 513 ml capacity with donor tubing 2 supplied with two needles, a roller clamp 14 and a flow controlling capillary 3 at its vertex. Bag 1 has the shape of a flattened cone when filled with blood, and is functioning as a blood separation chamber when held in a cavity of a correspondingly shaped rigid support (FIGS. 3, 4 and 6). The unit includes a round bag 4 filled with a displacing liquid such as buffered saline and a square bag 5 for collection of PRP which has eyelets 19 at its upper corners for hanging it by means of pins 36 on a rigid support (FIGS. 3,6 and 8). The unit includes a metal strip 6 having two key-hole slots 7 and 8 which clamp both flexible tubes coming from bag 1 and leading to the round bag 4 and bag 5. This strip also has a rectangular slot 9 for holding a latch. Both flexible tubes include pinch-clamps 10 and 11.

Figure 2:
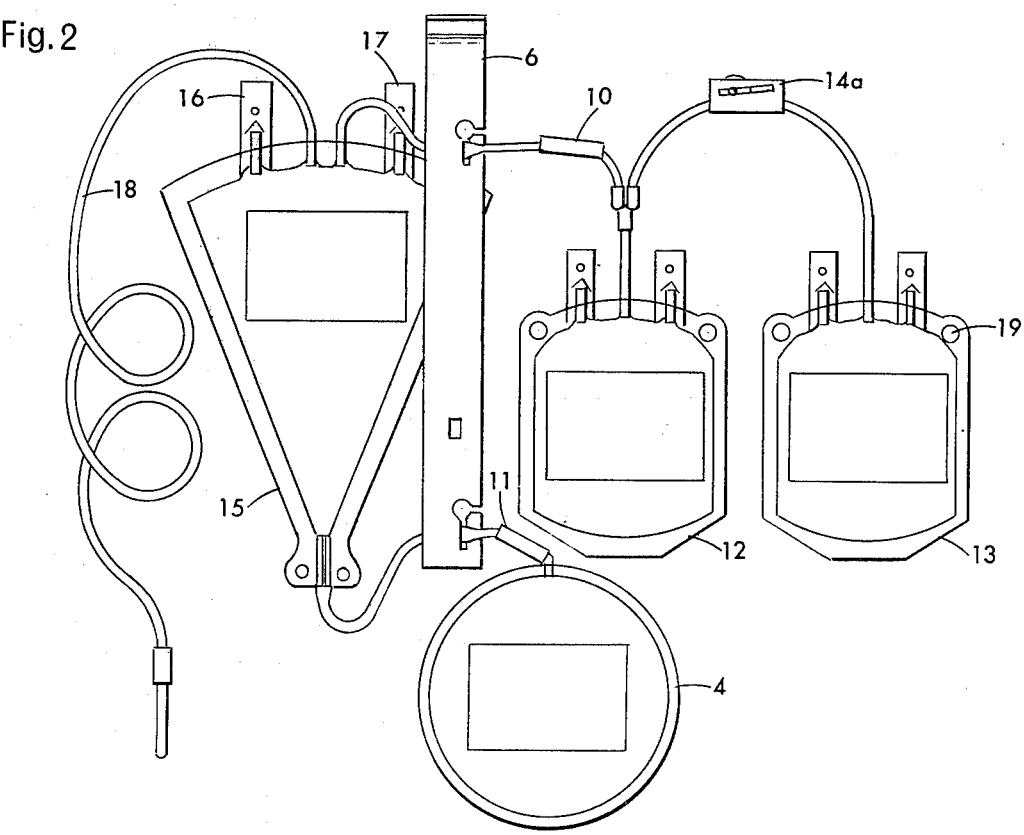
FIG. 2 is a side view of an embodiment of the disposable part of an apparatus consisting of a quadruple bag unit adapted for collection of blood platelets from multiple or random donors.
Figure 11:
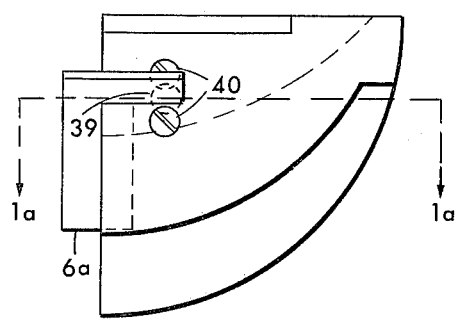
FIG. 11 is an upper front view of a portion of a flexible bag support incorporating another embodiment of a flow controlling valve mechanism.
Figure 13:
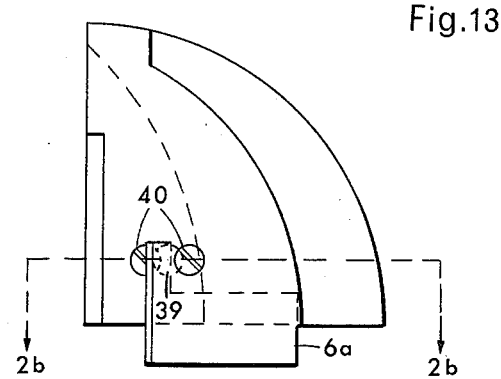
FIG. 13 is an upper front view of a portion of the support rotated 90° with respect to that shown in FIG. 11.

The apparatus for multiple donors, represented in FIG. 2, is a quadruple bag unit similar to that for a single donor (FIG. 1), except that it has two square bags 12 and 13, a roller clamp 14 on the tube connecting them, and that a triangular bag 15, has two sealed ports 16 and 17 needed for transfusion service. The donor tube 18 has only one needle instead of two used in the triple bag unit since there is no need for returning blood to the donor. Both square bags also have eyelets 19 at their upper corners for hanging them by means of pins 36 (FIGS. 3, 6 and 8) on a rigid support.

Figure 32:
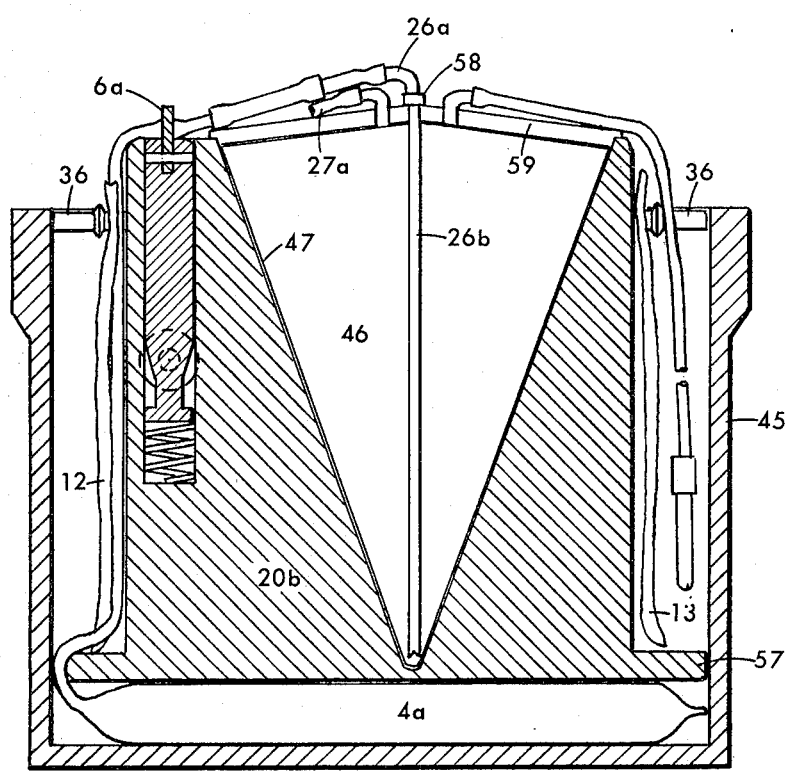
FIG. 32 is a cross-sectional view of a rectangular embodiment of the PRP separator placed in a correspondingly shaped centrifuge bucket taken along the line 1—1 of FIG. 33.
Figure 34:
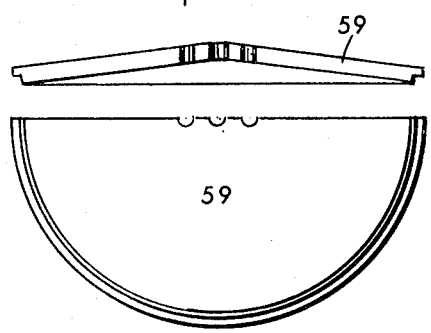
FIG. 34 is a side and top elevation view of one half of a circular lid covering conical chamber.

The rigid support shown in FIGS. 3 and 6 is designed for use with either triple or quadruple bag units. It consists of three parts 20, 21 and 22, where part 20 constitutes one-half of a support while quarter sections 21 and 22 form another half, all of which enclose a triangular bag 23 (FIGS. 3 and 4), representing either bag 1 or bag 15 (FIGS. 1 and 2), in the conical cavity 24 (FIG. 6). Donor tube 18 is hermetically sealed off at position 25 (FIG. 4) when bag 23 is filled with blood. Bag 23 has at both ends inlet and outlet tubes 26 and 27 (FIG. 4) which are held in grooves 28 and 28a in rigid support 22 (FIG. 6). Both inlet and outlet tubes 26 and 27 are kept closed by wedging them in key-hole slots 7 and 8 (FIGS. 1, 2 and 9). Strip 6 (FIGS. 1, 2 and 4) is placed in groove 30 (FIGS. 3 and 6) directed along a radial plane of a centrifuge swinging bucket between sections 21 and 22 (FIGS. 3,4 and 6). With the orientation of the rigid support 20 in the centrifuge bucket shown in FIG. 4, groove 30 is lying at an oblique angle to the longitudinal axis of support 20. In another embodiment support 20 is rotated 90° around its longitudinal axis from the above shown position. In the latter case, groove 30 is made parallel to the longitudinal axis of support 20, so that it is oriented in the direction of centrifugal force (FIGS. 32 and 34). Strip 6 is held in place by a latch mechanism 31 (FIGS. 6 and 9) engaging strip 6 by means of a rectangular slot 9 (FIGS. 1, 2, 9 and 10). Latch 31a is spring loaded and can retract and release strip 6 only when sufficient g force is applied to counterweight 32 (FIG. 10). The disengaged strip 6 slides down under centrifugal force against inlet and outlet tubes 26 and 27 which are held in place in grooves 28 and 28a (FIG. 6) and unclamps simultaneously both tubes 26 and 27, one of which (tube 26 is shown in FIG. 10. Opening fluid path 26 allows rigid support 20 together with parts 21 and 22 to slide down under centrifugal force inside a centrifuge bucket 33 (FIG. 4) and to compress bag 4, forcing medium to flow into bag 23 and displacing PRP via fluid path 27 into square bag 5 or 12 (FIGS. 1 and 2). Indentation 34 around the lower end of rigid supports 20, 21 and 22 (FIG. 4) serves to prevent pinching of bag 4 which supports 20, 21 and 22 push against bag 4. On one side of rigid support 20 there is a cylindrical insert 35 (FIGS. 4 and 6) which can be fitted with a handle, shown in FIG. 5, to serve as a plunger for expelling supernatant from bag 23. Retaining pin 29 keeps the plunger in place when the plunger is not in use. Square bags 12 and 13 are hung on pins 36 on rigid supports 20, 21 and 22 by means of eyelets 19 (FIGS. 3 and 8). In order to separate PPP from PC a dividing brace clamp 37 (FIG. 7) is inserted into holes 38 (FIGS. 6 and 8) which clamp bag 12, separating the liquid content into PC and PPP portions.

Figure 12:
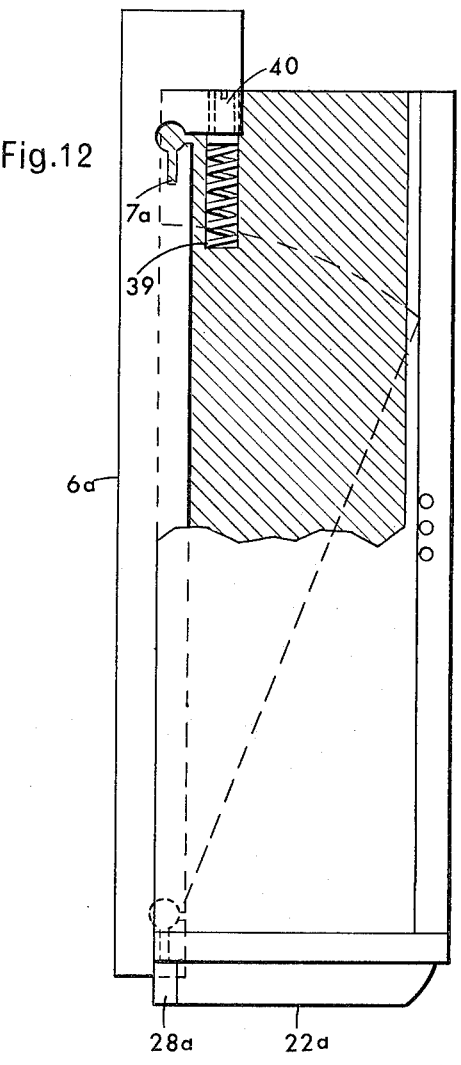
FIG. 12 is a partial cross-sectional side view of the above support taken along the line 1a—1a of FIG. 11 and in the plane along the line 2a—2a of FIG. 14.
Figure 14:
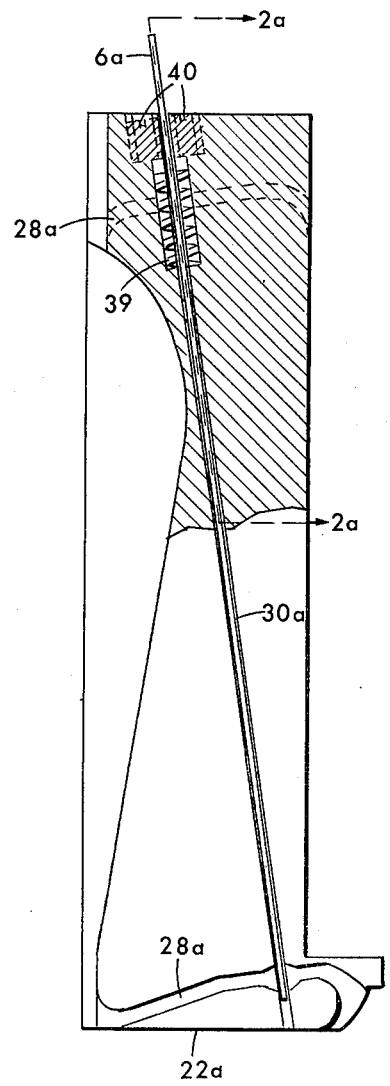
FIG. 14 is a partial cross-sectional side view of a support taken along the line 2b—2b of FIG. 13.

FIGS. 11 through 14 illustrate another possible embodiment of a valve mechanism actuated by a predetermined g force of a different design than that shown in FIGS. 9 and 10. As in the previous mechanism, this variation consists of a strip 6a with two key-hole slots 7a and 8a which can clamp or unclamp both flexible tubes 26 and 27 (FIGS. 4 and 9). Part of strip 6a along its length is positioned inside slot 30a in support sections 21 and 22a (FIGS. 6 and 11 through 14) in the direction along a radial plane of a centrifuge swinging bucket, so that strip 6a can slide down under the centrifugal force along 30a to unclamp the tubes 26 and 27 from the slots (FIG. 14). The upper part of strip 6a has a broad portion which rests on a spring 39 (FIGS. 12 and 14). The initial tension on the spring 39 is adjusted by means of two screws 40 so that strip 6a can move down and unclamp both tubes 26 and 27 only when the centrifugal force reaches a set g force (e.g., 230×g). The previous valve mechanism, shown in FIGS. 9 and 10, can only unclamp the tubes with the aid of the centrifugal force, whereas the present valve mechanism works in two ways. Under centrifugal force above 230×g, strip 6a compresses spring 39, slides down, thereby opening valve allowing flow of liquid. At a centrifugal force below 230×g spring 39 pushes strip 6a back to its original position, thereby stopping the flow by pinching the tube. The dual action of this mechanism has advantages in its application for the a multiple donor system by eliminating the need for clamps 10 and 11 (FIG. 2).

Harvesting of blood platelets with the new system is illustrated in two diagrammatic series of operational steps, one series for a single donor usage, shown in FIGS. 15 through 23, and the other series for multiple or random donor application, shown in FIGS. 24 through 31. In both of these series the assembled device is schematically shown in its vertical sectional view.

In the first operation step (FIG. 15) for single donor application, blood is drawn by phlebotomy into a triangular bag 1, functioning as a separation chamber, held inside an assembled support 20a. In the second step (FIG. 16), a roller clamp 14 on donor's tube 2 is closed and a support 20a together with a round bag 4 containing liquid medium (normal saline) is inserted into a centrifuge bucket 33. It is then subjected to centrifugation at about 90×g for 3 to 5 minutes to clear the top of bag 1 from red blood cells. In the third step (FIG. 17), the centrifugal force is increased to above 230×g which actuates the latch mechanism (FIGS. 9 and 10), unlatching strip 6 and simultaneously unclamping both inlet and outlet tubes 26 and 27. This allows the flow of liquid medium (normal saline) actuated by movement of support 20a under centrifugal force from bag 4 through tube 26 and capillary 3 (FIG. 4) into bag 1. The flow rate is controlled by a capillary tube 3 (FIG. 1) so that this flow of liquid can continue for about 3 to 5 minutes before bag 4 is empty. The capacity of bag 4 is about 300 ml. The controlled flow of liquid displaces PRP from bag 1 into a square bag 12 while red and white blood cells remain in bag 1. In the next step (FIG. 18), the centrifugal force is further increased to about 1000×g and centrifugation is allowed to continue for 8 to 12 minutes in order to separate PRP in square bag 12 into PC 41 and PPP 42 components. Thereafter (FIG. 19), support 20a is removed from centrifuge bucket 33, pinch clamp 10 on the tube connecting bag 12 to bag 1 is closed, and a brace clamp 37 is applied in order to separate PC from PPP in bag 12. Instead of using clamps 10 and 11 (FIG. 19), strip 6 (FIG. 1) can be pulled up manually to its initial position, which will clamp tubes 26 and 27. Next (FIG. 20), excess supernatant 43 above the blood fraction is expelled. This is accomplished by opening roller clamp 14, pulling out retaining pin 29, and then gradually depressing plunger 35 with the aid of handle 44 against bag 1. In the following step (FIG. 21), plunger 35 is pulled back into its original position and secured in place with retaining pin 29 while its handle 44 is removed. Clamp 10 is made to open and PPP 42 is expressed into bag 1 in order to reconstitute the packed blood cell fraction. Clamp 10 is closed manually, brace clamp 37 is pulled out and the triple bag system is removed from support 20a (FIG. 22). In the last step (FIG. 23), bag 1 is inverted and made ready for reinfusion of the reconstituted blood into the donor, while bag 12 is also ready for either immediate transfusion or storage of PC.

Harvesting of blood platelets by using the system designed for application with multiple donors involves less operational steps than with the above system. Since there is no need for the return of blood cells to the donor, reconstitution of packed blood cells with PPP is not required. The first five steps illustrated in FIGS. 24 through 28 are similar to those used in a single donor series except that donor tube 2 is hermetically sealed and severed after collection of blood (FIG. 25). Also, a liquid medium suitable for storage of red blood cells, such as citrate-phosphate-dextrose-adenine (CPDA), is used instead of normal saline for displacing PRP as in the single donor procedure. In the next step (FIG. 29), roller clamp 14a is open and PPP 41 is transferred from bag 12 into bag 13. Thereafter (FIG. 30), the quadruple bag system is removed from support 20a and all the connecting tubes are hermetically sealed and severed. Finally, this blood separation procedure results in three blood fractions (FIG. 31), PC and PPP in square bags 12 and 13, respectively, and the remaining blood cells suspended with CPDA medium in triangular bag 1. The red cell fraction collected in triangular bag 1 is ready for liquid storage without further manipulation.

Figure 33:
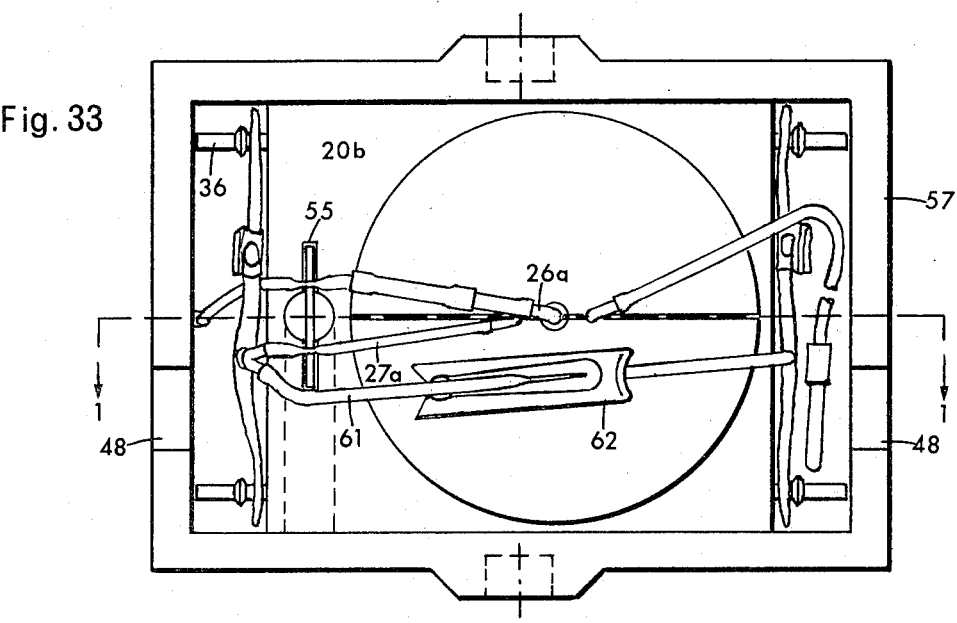
FIG. 33 is an upper front view of a rectangular embodiment of the PRP separator positioned in a rectangular centrifuge bucket.

FIGS. 32 through 39 illustrate a rectangular embodiment of the PRP separator contained in a rectangular centrifuge bucket 45 featuring a conical separation chamber 46. The apparatus consists of a rigid support 20b (FIGS. 32 and 33) for holding bag 47 in the conical chamber 46. Collection bags 12 and 13 of rectangular shape are positioned on both sides of the rigid support 20 by hanging them on two pins 36 (FIGS. 32 and 33). The inlet tube 26a and the outlet tube 27a can be clamped and unclamped simultaneously by means of two slot clamps made in a common plate 6a attached to rod 51. Rod 51 operates by centrifugal force and is controlled by a valve release mechanism (FIG. 38). Rod 51 has a tapered segment 52 which controls its sliding by a spring-loaded member 53. Rod 51 is oriented along a radial direction of a centrifuge rotor so that under the effect of centrifugal force at given r.p.m. the weight of rod 51 overcomes both the resistance of the spring-loaded member 53 and coil spring 54 and it slides down together with plate 6a. As a result, plate 6a is inserted into slot 55 thereby freeing tubes 26a and 27a from the slots in plate 6a. After the rotor comes to a stop coil spring 54 pushes rod 51 to its original position. Spring-loaded member 53 has a screw device 56 for adjustment of spring tension. The support 20b has at its bottom a rectangular flange 57 (FIGS. 32 and 33) which is used to compress a rectangular bag 4a, containing a displacement medium, by means of centrifugal force. The centrifuge bucket 45 has a see-through window 48 cut through both narrow sides of bucket 45 (FIGS. 33 and 37) allowing observation of the blood separation process using stroboscopic illumination during centrifugation. This arrangement permits the operator to maximize platelet collection from blood by controlling the duration of centrifugation. The window also permits installation of a photosensing device for automatic control of blood separation. FIG. 36 illustrates an H-shaped centrifuge rotor 50 with two swinging buckets 45, and each bucket is fitted with a PRP separator unit. The inlet tube 26a is sealed at the center of base and it extends into the conical bag close to its apex. This central inlet tube 26b is anchored by a rim 58 to the lid 59 (FIGS. 32 and 34).

Figure 40:
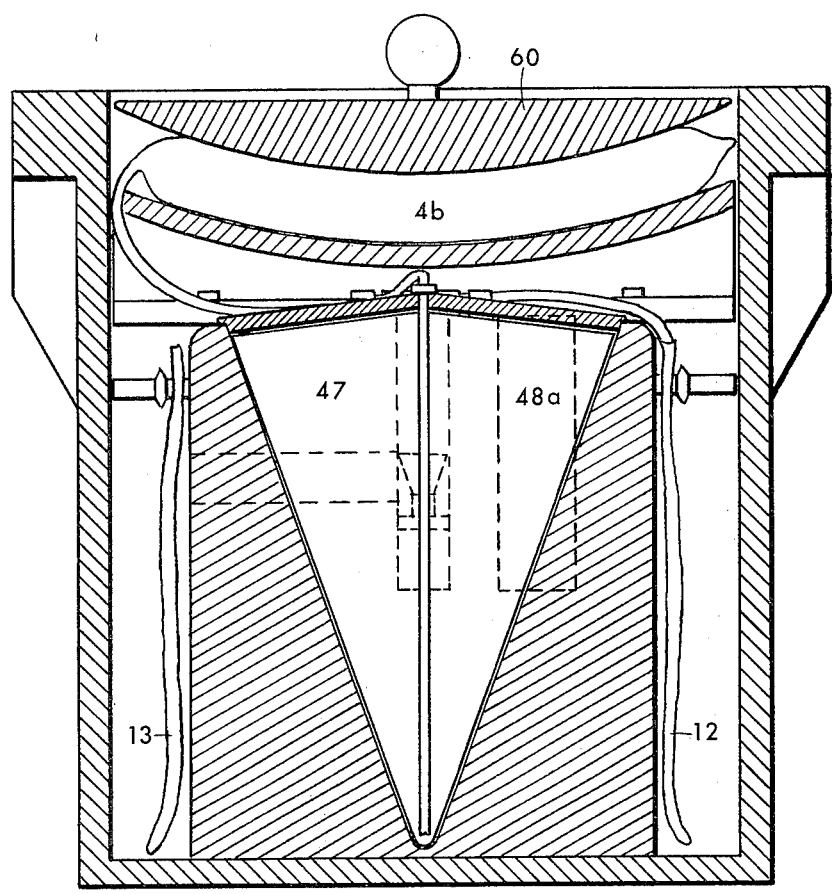
FIG. 40 is a cross-sectional view of another rectangular embodiment of the PRP separator positioned in a rectangular centrifuge bucket taken along the line 1a—1a of FIG. 41.
Figure 41:
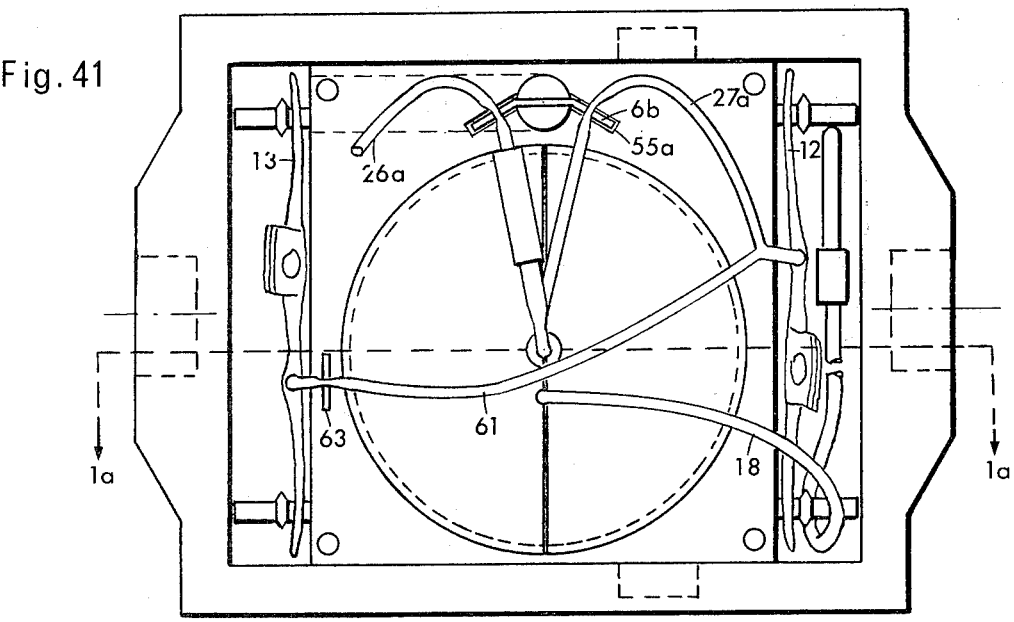
FIG. 41 is a top view of a rectangular embodiment of the PRP separator positioned in a rectangular centrifuge bucket showing the bag containing displacing liquid medium and its support.

FIGS. 40 and 41 illustrate another embodiment of a PRP separator which employs a different mechanism for generating flow of displacing medium from bag 4b into conical bag 47. Instead of subjecting bag 4b containing displacing medium to the full weight of the whole separator unit (FIG. 32) during centrifugation to induce liquid flow, in the present embodiment the flow is generated by the differences of the fluid levels between bag 4b and bag 12. This is accomplished by placing bag 4b above conical bag 47 so that bag 4b is closer to the center of rotation than bags 47 and 12. The fluid flow can be increased, if needed, by placing above bag 4b a weighted plate 60 which compresses bag 4b with the aid of centrifugal force. The valve controlling mechanism of this embodiment is similar to that shown in FIG. 38 except that plate 6b has a bent configuration as shown in FIG. 41 in order to conveniently accommodate the inlet and outlet tubings 26a and 27a (FIG. 41). Tube 61, connecting bags 12 and 13, is closed by inserting the tube into a stationary wedge clamp 63 (FIG. 41) attached to support 20b instead of using a wedge clamp not attached to the support 20b as shown in FIG. 33. The disposable bag system shown in FIG. 35 is different from that shown in FIG. 2 in that the present system contains a large square bag 4a of 513 ml. capacity, a conical bag 47 of the same capacity and the system is provided with a centrally located inlet tube 26a extending inward from the base towards the apex of bag 47. A short capillary tube insert 64 (detailed in FIG. 39) and an appendage 65 filled with saline and connected to the donor tube 18a while using the same collection bags 12 and 13 as in FIG. 2. This appendage is used to rinse the donor tube free of blood. The large bag 4a is used not only for holding displacing medium but also for storage of residual blood cells which are being transferred from bag 47 after the separation of PRP is completed. The capillary 64 (FIG. 39) controlling liquid flow through inlet tube 26a (FIGS. 35 and 39) is dislodged into a compartment 66 having a larger diameter than inlet tube 26a as shown in FIG. 39 in order to allow rapid flow of residue blood cells during transfer from bag 47 into bag 4a.

The advantages of this embodiment are that:

(a) bag 4b is not subjected during centrifugation to the excessive weight of the whole separator unit;

(b) it allows one to control hydrostatic pressure in bag 4b by using different weighted plates 60;

(c) it permits less change of momentum in the bucket than that of the design shown in FIG. 32;

(d) the stationary separation chamber 4b facilitates both visual and automated monitoring through window 48a; and (e) the view of bag 4b through window 48b is not obstructed by bags 12 and 13.

Figure 42:
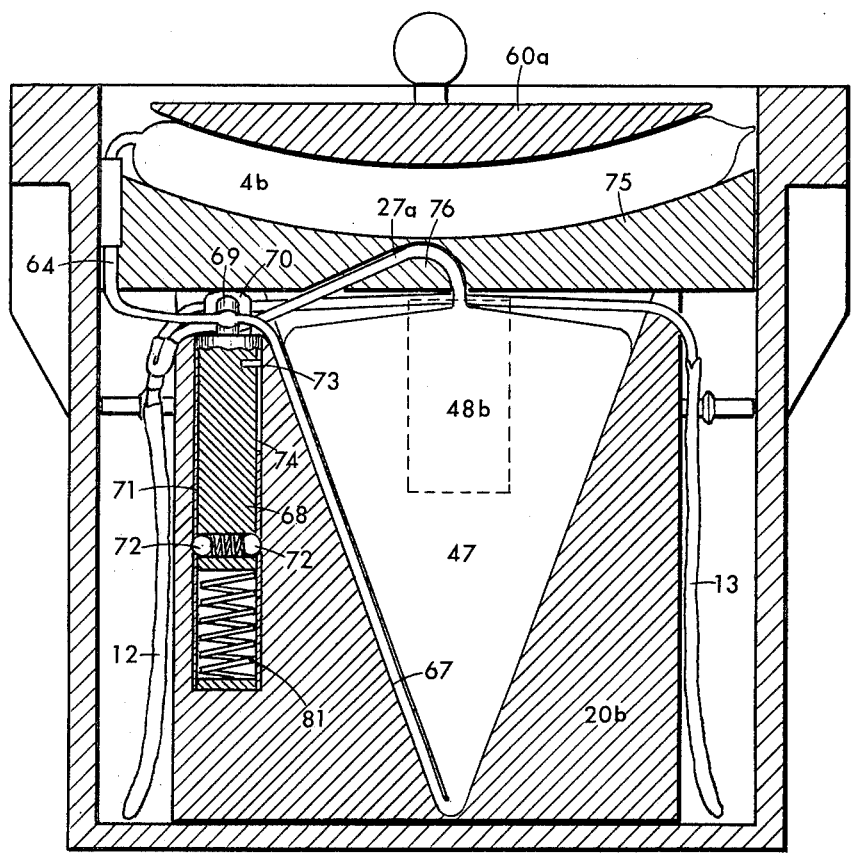
FIG. 42 is a cross-sectional view of a preferred embodiment of the PRP separator designed for a rectangular centrifuge bucket.
Figure 43:
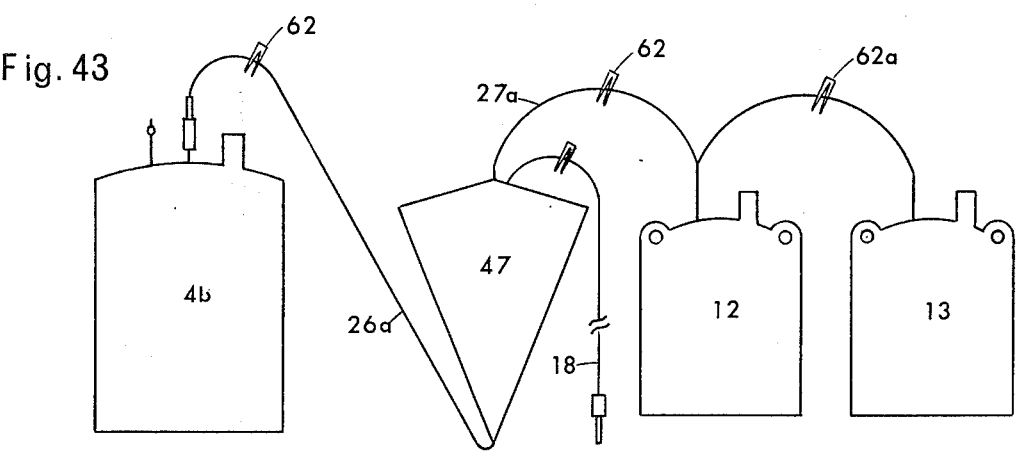
FIG. 43 is a schematic representation of a preferred embodiment of a disposable quadruple-bag unit for harvesting of blood platelets.
Figure 48:
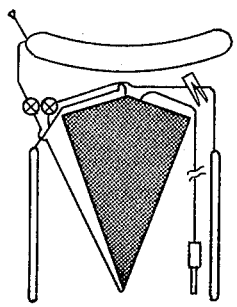
FIG. 48 is a cross-sectional diagramatic view of an apparatus containing a quadruple bag unit for multiple donors taken along a verticle central axis and showing a conical bag being filled with blood. The rigid support is not shown.
Figure 49:
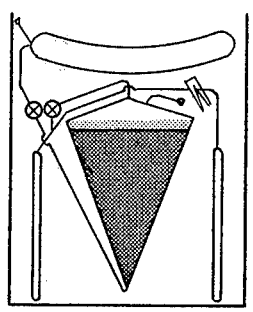
FIG. 49 is the same apparatus as above inserted into a centrifuge bucket and showing clearance at the top of a conical bag and a thin layer of PRP after slow-speed centrifugation.
Figure 50:
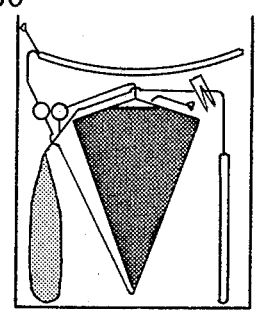
FIG. 50 is the same apparatus as above after centrifugation at a higher speed than in the preceding step showing both fluid lines leading to and from a conical bag being open, and showing big square bag empty, and PRP displaced from the conical bag into a square bag on the left.
Figure 51:
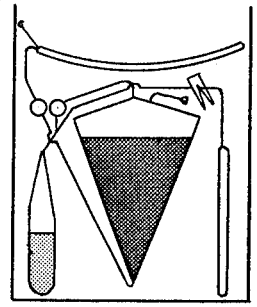
FIG. 51 is the same apparatus as above after centrifugation at a highest speed showing separation of PRP into PC and PPP in the bag.
Figure 52:
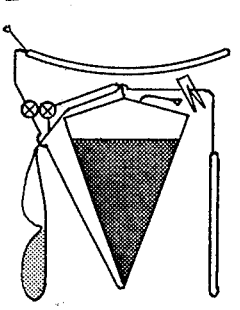
FIG. 52 is the same apparatus as above removed from a centrifuge bucket and having a square bag clamped in the mid-portion to separate PPP from PC while a fluid line coming from a conical bag and joining with two square bags is being closed.
Figure 53:
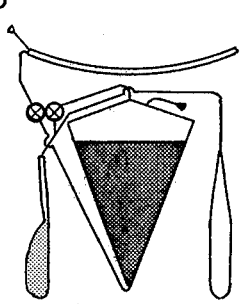
FIG. 53 is the same apparatus as above after PPP has been transferred to a square bag on the right side.

Another embodiment of the PRP separator illustrated in FIG. 42 provides attachment of inlet tube 26a directly to the apex of conical bag 47 shown in a schematic representation of FIG. 43. The outlet tube 27a is attached at the center of the base of bag 47 (FIG. 42 and 43). In this embodiment no lid is used such as that shown in FIGS. 32, 34 and 40. In order to accommodate the inlet tube 26a running along one side of bag 47, a straight groove 67 is provided along the wall of the conical chamber in the support 20b. As in the design shown in FIGS. 40 and 41, the flow of liquid medium into bag 47 is generated by differences in hydrostatic pressure between the fluid levels of bag 4b and bag 12. Another novel feature of this embodiment is the design of the valve control mechanism 68 (FIG. 42). It consists of a movable spring-loaded rod 68 having a central pin 69 at its upper end which is positioned between two stationary supporting members 20 attached to the jacket 71 holding the rod 68. The tubes 26a and 27a are clamped by forcing them manually between the central pin 69 and the two supporting members 70 (FIG. 44). Rod 68 is held in place by two spring-loaded steel balls 72 fitting in corresponding retaining holes in the jacket. Guided by pin 73 and slot 74 cut in the jacket, the valve control mechanism is actuated by centrifugal force at a prescribed g force when the spring-loaded balls 72 are forced out of the retaining holes causing release of rod 68 which in turn pushes down against spring 81 and at the same time pulls the central pin 69 away from the supporting members 70 thereby unclamping tubes 26a and 27a. Square bag 4b rests on a supporting plate 75 having the curvature of an arc formed by the radius of rotation. The flow regulating capillary tube arrangement 64 as shown in FIG. 39 is supported in a cut-out passage-way made in plate 75. Tube 27a is supported by inserting it into the slot behind the member 76 as shown in FIG. 42.

The disposable quadruple unit of bags is shown in the schematic representation of FIG. 43. Clamps 62 keep tubes 26 and 27a closed until the bags are placed into support 20b and both tubes 26a and 27a are clamped by inserting them on both sides of pin 69. Clamp 62a is removed prior to transferring of PPP from bag 12 to bag 13. A rectangular window 48b (FIG. 42) is provided for visual monitoring of PRP separation.

Figure 54:
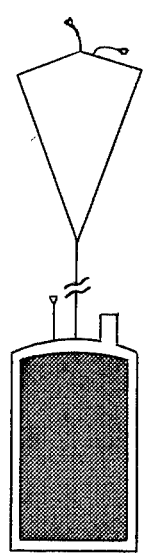
FIG. 54 is showing transfer of residual blood from the conical bag into a large square bag.
Figure 55:
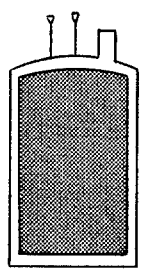
FIG. 55 is a side view of a disconnected and hermetically sealed large square bag containing blood ready for storage.
Figure 56:
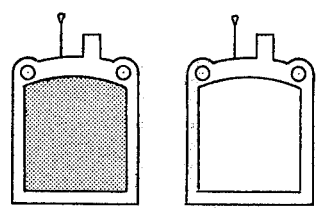
FIG. 56 is a side view of two disconnected square bags, one containing PC and the other PPP.

The operational steps in the rectangular embodiment of FIGS. 42 and 43 for multiple donor application are illustrated diagrammatically in a series of figures from 48 through 56. The steps shown in FIGS. 48 through 53 and 56 are similar to those shown in FIGS. 24 through 29. The steps of FIGS. 54 and 55 are different in that the residual blood cells in conical bag are transferred into large square bag previously occupied by displacing medium. Then the large bag is severed from the conical bag and is hermetically sealed for storage.

FIGS. 44 through 47 illustrate another version of the PRP separator adapted particularly for procuring small volumes of PRP for laboratory use. The main novel feature of this embodiment is the design of the disposable triple-bag unit (FIG. 47) made of two plastic sheets sealed together which also form flat connecting tubings 26b and 27b and appendages 77 and 78 for filling bags 4c and 47a, respectively. Filling of these bags is accomplished by puncturing these appendages with a needle and then resealing them. Tube 26b has a narrow capillary portion 79 which regulates the rate of liquid flow between bag 4c and bag 47a. Clamps 62 are used until the unit is secured in the support 20c. Tubes 26b and 27b are inserted on both sides of pin 69 (FIGS. 44 and 45) to clamp them. Tube 27b is supported by a slot 80 behind the member 76 made in the supporting plate 75 (FIG. 46). Bag 4c rests on plate 75 and is covered by a weighted plate 60a which provides the necessary pressure against bag 4c during centrifugation. Bag 12a is attached to one side of support 20c by means of two pins 36.

The operational steps with this embodiment of a PRP separator are similar to those shown in FIGS. 15 through 31, except that the bag containing displacing medium is positioned above the separation bag instead of being underneath it.

Figure 57:
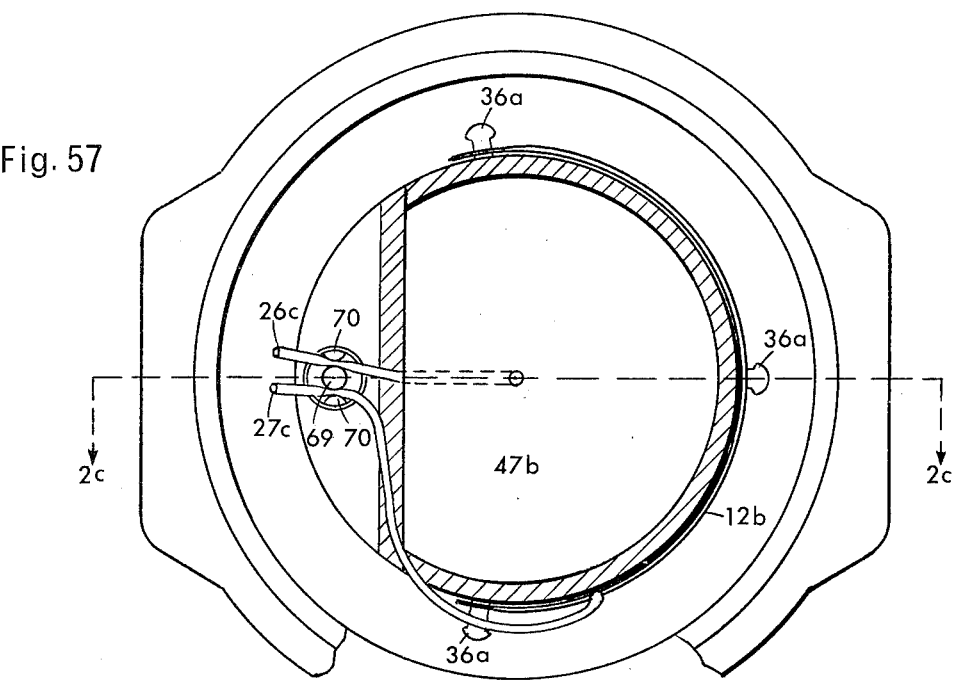
FIG. 57 is a horizontal cross-sectional view of another embodiment of the PRP separator designed for a cylindrical centrifuge bucket incorporating a new fluid displacement system taken along the line 1c—1c of FIG. 58.
Figure 58:
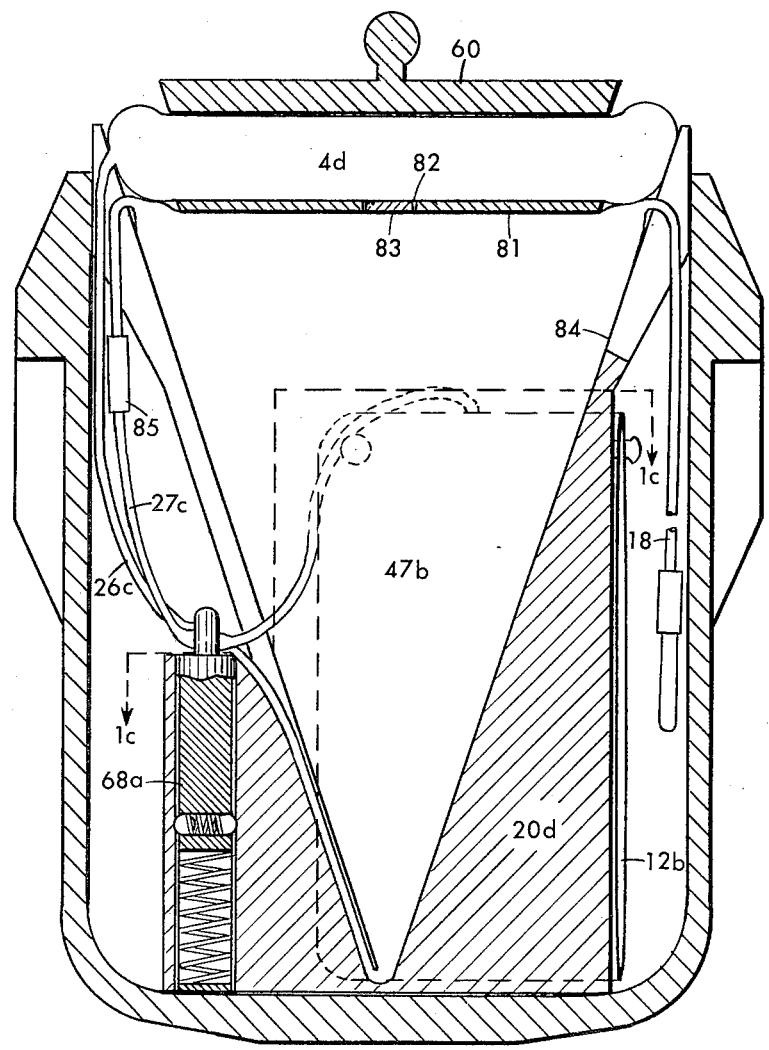
FIG. 58 is a vertical cross-sectional view of the PRP separator within a cylindrical centrifuge bucket taken above the line 2c—2c of FIG. 57.

FIGS. 57 and 58 show another preferred embodiment of a PRP separator which provides a different mechanism for displacing PRP from the blood separation chamber. According to this design, after the initial separation of PPP and PRP in conical bag 47b at a low speed centrifugation, the centrifugal speed is increased sufficiently to achieve optimum PRP separation at which point the valve control mechanism 68a is actuated allowing flow through inlet and outlet tubings 26a and 26c, respectively. A flow regulating device 85 is incorporated on-line of tube 27c. In contrast to previous designs of FIGS. 40, 42 and 45, bag 4d rests directly on the flat top of the conical bag 47b, being separated from it only by a thin metal plate 81 which has a centering hole 82. A central knob 83 attached to the surface of the bag 47b is fitted into hole 82. Under the pressure exerted by the combined weight of bag 4d, weighted plate 60 and plate 81 in response to centrifugal force, bag 47b slowly collapses and PPP and PRP is being displaced from the upper part of chamber 47b via tube 27c into the collection bag 12b which is attached to the rigid support 20d by means of three pins 36a. Plate 81 stops at a specified level inside the rigid cone 84 thereby limiting displacement of liquid from bag 47b. The maximum useful volume of PRP displacement from bag 47b is being determined by the hematocrit of the respective blood sample. Once the hematocrit of blood is measured, plate 81 of appropriate diameter is selected in order to control the displacement volume.

It is important to note that at the same time as PPP and PRP are being displaced from the top of the chamber 47b, the medium from bag 4d displaces PRP from blood contained in the lower part of conical chamber 47b as in the previous designs of FIGS. 40, 42 and 45. As a result of these two converging actions, there is miminum dilution of separated PRP with the displacing medium (normal saline).

This design allows maximum utilization of space in the 1 liter cylindrical centrifuge bucket so that 260 ml. of blood can be processed by this device.

Since many changes can be made in the construction of the above PRP separation apparatus and different embodiments of this invention can be provided without departing from the scope thereof, it is intended that all matter contained in the above description or shown in the accompanying drawings shall be interpreted as illustrative and not in a limiting sense.

What is claimed is:

1. An improved separator, adapted to separate the particles from the liquid of a fluid sample, wherein said separator comprises:
   a body adapted to be subjected to centrifugal force and containing a first cavity adapted to receive a volume of displacing liquid therein, and a second cavity adapted to receive a volume of particle rich liquid of said fluid;
   said body containing a centrifugal chamber having centrifugally inner and outer ends, and containing said fluid sample from which particles are to be separated, and injection passageway means for movement of displacing liquid from said first cavity to said outer end of the chamber;
   a discharge passageway means at said inner end of the chamber for discharging particle rich liquid into said second cavity in response to injection of displacing liquid into the chamber; and
   said second cavity positioned substantially centrifugally outwardly from said inner end of said chamber such that in response to centrifugal force on said body said particles are separated from the liquid of said particle rich liquid in said second cavity without substantial counterflow back into the chamber.

2. The separator of claim 1 further comprising latching means having two apertures adapted to receive said discharge passageway means and said injection passageway means;
   said latching means adapted to move to open simultaneously said discharge and injection passageway means in response to centrifugal force on said body.

3. The separator of claim 2 further comprising spring bias means;
said latching means urged against said spring bias means such that said latching means moves to open said passageway means in response to a centrifugal force on said body sufficient to overcome the force of said spring bias means.

4. The separator of claim 3 further comprising a plunger means, said plunger means adapted to move to displace a volume from said chamber.

5. The separator of claim 3 wherein said chamber is substantially conically chaped.

6. The separator of claim 5 wherein said body is substantially in the shape of a rectangular solid and said body has a window means for viewing said chamber.

7. The separator of claim 6 wherein said chamber is contained in a piston and said piston is adapted to move into the first cavity in response to centrifugal force on said body.

8. The separator of claim 6 wherein said first cavity is positioned near the outer end of said chamber substantially near the center of rotation of said chamber.

9. The separator of claim 8 further comprising weight means placed above said first cavity and adapted to move into said cavity in response to centrifugal force on said body.

10. The separator of claim 9 wherein said weight means and said first cavity are adapted to move into said chamber in response to centrifugal force on said body.

11. The separator of claim 10 wherein said weight means is circular in shape, and is adapted to move a specified distance into said chamber, displacing a predetermined volume of fluid.

12. The separator of claim 1 characterized further by the inclusion of a blood sample in said chamber.

13. A method of separating PC, PPP from a blood sample, wherein said blood sample is supported in a centrifugal chamber having an inner and an outer end, an injection passageway means from a first cavity to said outer end, a discharge passageway means from said inner end to a second cavity, said second cavity positioned substantially centrifugally outwardly from said inner end of said chamber, said method comprising:
supporting said sample in said chamber;
subjecting said chamber to an initial centrifugal force of at least a predetermined amount to stratify red cells in the sample away from the inner end;
subjecting said chamber to a second centrifugal force while (1) injecting into the outer end of the chamber a displacing liquid from said first cavity at a predetermined volume and flow rate, and (2) displacing PRP from the inner end of the chamber into the second cavity, as the displacing liquid is injected from the first cavity by the second centrifugal force on the blood sample; and
subjecting said second cavity to a third centrifugal force sufficient to separate PRP into PC at one end and PPP at another end.

14. The method of claim 13 further comprising latching to open simultaneously said injection and discharge passageways means upon application of said second centrifugal force.

15. The method of claim 13 further comprising transferring said PPP from said second cavity into a transfer bag means.

* * * * *